United States Patent

Umemura et al.

[11] Patent Number: 5,883,089
[45] Date of Patent: Mar. 16, 1999

[54] CEPHEM DERIVATIVES

[75] Inventors: Eijiro Umemura; Kunio Atsumi, both of Yokohama; Katsuyoshi Iwamatsu; Atsushi Tamura, both of Yokohama, all of Japan

[73] Assignee: Meiji Seika Kabushiki Kaisha, Tokyo to, Japan

[21] Appl. No.: 750,945

[22] PCT Filed: May 24, 1996

[86] PCT No.: PCT/JP96/01406

§ 371 Date: Apr. 3, 1997

§ 102(e) Date: Apr. 3, 1997

[87] PCT Pub. No.: WO94/37499

PCT Pub. Date: Nov. 28, 1996

[30] Foreign Application Priority Data

May 25, 1995 [JP] Japan ..................... 7-126090

[51] Int. Cl.$^6$ .................... C07D 501/56; A61K 31/545
[52] U.S. Cl. ............................ 514/205; 540/227
[58] Field of Search ................ 540/227; 514/205

[56] References Cited

FOREIGN PATENT DOCUMENTS

| 0551034 | 7/1993 | European Pat. Off. . |
|---|---|---|
| 1-261391 | 10/1989 | Japan . |
| WO 95/07912 | 3/1995 | WIPO . |
| WO96/05205 | 2/1996 | WIPO . |

Primary Examiner—John M. Ford
Attorney, Agent, or Firm—Wenderoth, Lind & Ponack, L.L.P.

[57] ABSTRACT

Compounds, represented by the following formula (I), having a β-(substituted or unsubstituted imidazo[5,1-b]thiazolyl)vinyl group at the 3-position of the cephem ring and a salt and an ester thereof are disclosed. The compounds have antibacterial activity against a very wide spectrum of bacteria and potent antibacterial activity against Gram-positive bacteria, Gram-negative bacteria, and resistant bacteria.

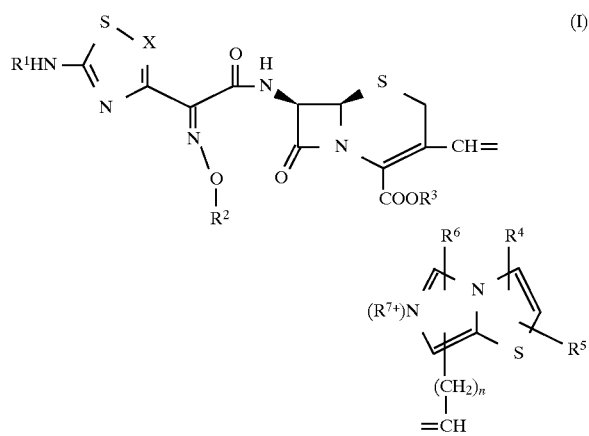

wherein X represents CH or N, $R^1$ represents a hydrogen atom or an amino protective group, $R^2$ represents a hydrogen atom, a $C_{1-6}$ alkyl group, a $C_{3-7}$ cycloalkyl group, or a hydroxy protective group, $R^3$ is absent or represents a hydrogen atom, a salt forming cation, or a carboxyl protective group, $R^4$, $R^5$, and $R^6$, which may be the same or different, each independently represent a hydrogen atom or a $C_{1-6}$ alkyl group, $R^{7+}$ is absent or a cation of a $C_{1-6}$ alkyl, and n is an integer of 0 to 1.

11 Claims, No Drawings

CEPHEM DERIVATIVES

This is a 371 of PCT/JP96/01406 filed May 24, 1996.

BACKGROUND OF THE INVENTION

1. Field of the Invention

The present invention relates to novel β-lactam antibiotics and pharmaceutically acceptable salts and esters thereof. More particularly, the present invention relates to novel cephem compounds having antibacterial activity and pharmaceutically acceptable salts and esters thereof.

2. Background Art

Cephem antibiotics exhibit excellent antibacterial activity with low toxicity for mammals. They are therefore very important to the treatment of infectious diseases in mammals. In recent years, cephem derivatives having an aminothiazolylacetyl group at the 7-position of the cephem ring have been found to have potent antibacterial activity and stability against β-lactamase, leading to numerous studies and developments in these cephem derivatives. Various semi-synthetic cephem compounds have already been put on the market and clinically used as therapeutic agents for various infectious diseases.

However, among these compounds, those usable as a therapeutic agent having antibacterial activity against Pseudomonas aeruginosa and Myxomycetes are limited. Further, these compounds are unstable against β-lactamase produced by resistant bacteria and have drawbacks such as low antibacterial activity against the resistant bacteria which have posed a clinical problem these days. Furthermore, many cephem antibiotics have been developed for use in injections, and it is often pointed out that, in the case of oral administration, the cephem antibiotics have low absorption ratio and, hence, have unsatisfactory efficacy.

Specific examples of β-lactam compounds known in the art include Cefixime, Cefdinir, ME 1207 (Cefditren pivoxil), and ME 1206 (Cefditren).

However, no compounds having a β-substituted vinyl side chain, especially a β-(substituted or unsubstituted imidazo[5,1-b]thiazolyl)vinyl group, at the 3-position of the cephem ring have been reported so far as the present inventors know.

SUMMARY OF THE INVENTION

The present inventors have now found that compounds having a β-(substituted or unsubstituted imidazo[5,1-b] thiazolyl)vinyl group at the 3-position of the cephem ring have antibacterial activity against a very wide spectrum of bacteria and potent antibacterial activity against Gram-positive bacteria, Gram-negative bacteria, and resistant bacteria.

Thus, an object of the present invention is to provide novel cephem derivatives having potent antibacterial activity against a wide spectrum of bacteria.

Another object of the present invention is to provide pharmaceutical compositions comprising the cephem derivative of the present invention.

A further object of the present invention is to provide a method for treating infectious diseases, comprising the step of administering the cephem derivative of the present invention.

The compounds according to the present invention are cephem derivatives represented by the following formula (I):

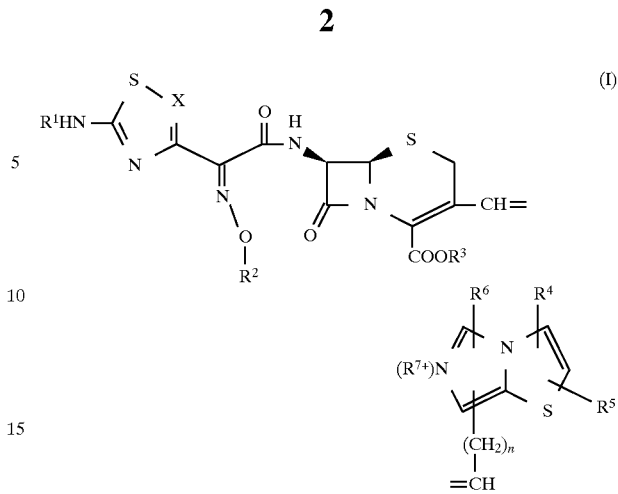

wherein X represents CH or N, $R^1$ represents hydrogen or an amino protective group, $R^2$ represents hydrogen; $C_{1-6}$ alkyl in which one or more hydrogen atoms may be substituted by halogen, carboxyl, $C_{1-4}$ alkoxycarbonyl, carbamoyl, N-$C_{1-4}$ alkylcarbamoyl, cyano, amino, or $C_{1-4}$ alkylamino; $C_{2-4}$ alkenyl; $C_{2-4}$ alkynyl; $C_{3-7}$ cycloalkyl; or a hydroxy protective group, $R^3$ is absent or represents hydrogen, a salt forming cation, or a carboxyl protective group, $R^4$, $R^5$, and $R^6$, which may be the same or different, each represent
hydrogen;
$C_{1-4}$ alkoxy;
$C_{1-4}$ alkylthio;
cyano;
carboxyl;
$C_{1-4}$ alkoxycarbonyl;
carbamoyl;
N-$C_{1-4}$ alkylcarbamoyl;
formyl;
amino in which one or more hydrogen atoms may be substituted by formyl, $C_{1-4}$ alkylcarbonyl, or $C_{1-4}$ alkylsulfonyl;
halogen;
$C_{1-6}$ alkyl in which one or more hydrogen atoms may be substituted by a group selected from the group consisting of hydroxyl, $C_{1-4}$ alkoxy, mercapto, $C_{1-4}$ alkylthio, cyano, halogen, carboxyl, $C_{1-4}$ alkoxycarbonyl, carbamoyl, N-$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, halogen-substituted $C_{1-4}$ alkylcarbonylamino, carbamoyloxy, N-$C_{1-4}$ alkylcarbamoyloxy, $C_{1-4}$ alkylsulfonylamino, ureido, N-$C_{1-4}$ alkylureido, $C_{1-4}$ alkylcarbonylamino, and imino-$C_{1-4}$ alkylamino;
$C_{3-6}$ cycloalkyl;
$C_{2-4}$ alkenyl; or
$C_{2-4}$ alkynyl or
any two of $R^4$, $R^5$, and $R^6$ may together represents $C_{3-6}$ alkylene where one or more methylene groups in this alkylene group may be replaced by —NH—, —O—, —S—, or —CO—, $R^{7+}$ is absent or represents a cation of $C_{1-6}$ alkyl, substituted $C_{1-6}$ alkyl, or substituted $C_{1-6}$ alkylene, and n is an integer of 0 to 1; and pharmaceutically acceptable salt and ester thereof.

The compounds represented by the formula (I) have antibacterial activity against a very wide spectrum of bacteria and potent antibacterial activity against Gram-positive bacteria, Gram-negative bacteria, and resistant bacteria. The antibacterial activity of these compounds is superior to that of Cefixime, Cefdinir, and ME 1206 having chemical structures analogous to that of the compounds of the present invention. In particular, the compounds of the present invention have very potent antibacterial activity against *Staphylococcus aureus* (MSSA and MRSA) and Enterococcus (faecalis).

DETAILED DESCRIPTION OF THE INVENTION

Definitions

As used herein, the term "alkyl" as a group or a part of a group means a straight or branched chain. Specific examples thereof include methyl, ethyl, propyl, iso-propyl, n-butyl, iso-butyl, and t-butyl. The term "halogen" means a fluorine, chlorine, bromine, or iodine atom. The term "aryl" preferably means phenyl, naphthyl, and tolyl.

Compounds

In the formula (I), the protective group, for an amino group, represented by $R^1$ is preferably a group which can be easily removed by acid hydrolysis or the like. Specific examples thereof include alkoxycarbonyl groups, such as a t-butoxycarbonyl group, acyl groups, such as formyl and chloroacetyl groups, and a trityl group.

In the formula (I), the hydroxy protective group represented by $R^2$ may be, for example, a trityl, t-butyldimethylsilyl, trimethylsilyl, triethylsilyl, allyloxycarbonyl, p-methoxybenzyloxycarbonyl, or p-nitrobenzyloxycarbonyl group. Preferred examples of $R^2$ include $C_{1-6}$ alkyl (more preferably, $C_{1-4}$ alkyl) and halogen-substituted $C_{1-6}$ alkyl (more preferably, halogen-substituted $C_{1-4}$ alkyl) groups and hydroxy protective groups (for example, trityl, methoxymethyl, methoxyethoxymethyl, formyl, and tetrahydropyranyl groups).

In the formula (I), when $R^3$ is absent, the carboxyl group, to which $R^3$ is attached, may be free —COO⁻ or, when $R^{7+}$ described below is present, may form an intramolecular salt. Preferred examples of the salt-forming cation represented by $R^3$ include cations of an alkali metal salt, an alkaline earth metal salt and an ammonium salt. The carboxyl protective group represented by $R^3$ may be a protective group generally used for cephalosporin. Preferred examples thereof include aryl, lower alkyl, lower alkoxymethyl, lower alkylthiomethyl, lower alkanoyloxymethyl, lower alkoxycarbonyloxyalkyl, lower alkylcarbonyloxyalkyl, and optionally substituted (2-oxo-1,3-dioxolen-4-yl)methyl groups. Metabolically unstable protective groups which can be hydrolyzed in vivo and removed are particularly preferred. Specific examples of such protective groups include lower alkoxymethyl, lower alkylthiomethyl, lower alkanoyloxymethyl, lower alkoxycarbonyloxyalkyl, lower alkylcarbonyloxyalkyl, and optionally substituted (2-oxo-1, 3-dioxolen-4-yl)methyl groups.

There is no particular limitation on the position of the imidazo[5,1-b]thiazolyl group which is attached to a vinyl group present in the 3-position of the cephem skeleton. However, the 2-, 3-, 5-, or 7-position of the imidazo[5,1-b] thiazolyl group is preferred.

At least one hydrogen atom on the imidazo[5,1-b] thiazolyl group may be substituted. The substituents are represented by $R^4$, $R^5$, and $R^6$ in the formula (I). $R^4$, $R^5$, and $R^6$ may be the same or different and each represent hydrogen; $C_{1-4}$ alkoxy; $C_{1-4}$ alkylthio; cyano; carboxyl; $C_{1-4}$ alkoxycarbonyl; carbamoyl; N-$C_{1-4}$ alkylcarbamoyl; formyl; amino in which one or more hydrogen atoms may be substituted by formyl, $C_{1-4}$ alkylcarbonyl, or $C_{1-4}$ alkylsulfonyl; halogen; $C_{1-6}$ alkyl in which one or more hydrogen atoms may be substituted by group selected from the group consisting of hydroxyl, $C_{1-4}$ alkoxy, mercapto, $C_{1-4}$ alkylthio, cyano, halogen, carboxyl, $C_{1-4}$ alkoxycarbonyl, carbamoyl, N-$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, halogen-substituted $C_{1-4}$ alkylcarbonylamino, carbamoyloxy, N-$C_{1-4}$ alkylcarbamoyloxy, $C_{1-4}$ alkylsulfonylamino, ureido, N-$C_{1-4}$ alkylureido, $C_{1-4}$ alkylcarbonylamino and imino-$C_{1-4}$ alkylamino); $C_{3-6}$ cycloalkyl; $C_{2-4}$ alkenyl; or $C_{2-4}$ alkynyl. Any two of $R^4$, $R^5$, and $R^6$ may together represent $C_{3-6}$ alkylene, where one or more methylene groups in this alkylene group may be substituted by —NH—, —O—, —S—, or —CO—. When $R^4$, $R^5$, and $R^6$ represent halogen, the halogen atom is preferably a fluorine or chlorine atom. The position of these substituents $R^4$, $R^5$, and $R^6$ is preferably the 2-, 3-, 5-, and 7-positions of the imidazo[5,1-b] thiazolyl group.

According to a preferred embodiment of the present invention, a group of compounds having $C_{1-6}$ alkyl (more preferably, $C_{1-4}$ alkyl) or halogen-substituted $C_{1-6}$ alkyl (more preferably, halogen-substituted $C_{1-4}$ alkyl) at the 2-, 3-, 5-, and 7-positions is preferred.

A preferred group of compounds according to the present invention are those wherein the hydrogen atom at the 2-, 3-, 5-, or 7-position of the imidazo[5,1-b]thiazole is attached to the vinyl group present at the 3-position of the cephem skeleton and the hydrogen atom at any one of the remaining positions is substituted by a methyl, ethyl, n-propyl, iso-propyl, n-butyl, iso-butyl, sec-butyl, tertbutyl, fluoromethyl, difluoromethyl, 1-fluoroethyl, 1,1-difluoroethyl, 2-fluoroethyl, 2,2-difluoroethyl, 2-chloroethyl, or 2,2-dichloroethyl group.

In the formula (I), when $R^{7+}$ is present, the compounds represented by the formula (I) have a positive charge at the 6-position of the imidazo[5,1-b]thiazolyl group. As described above, this charge may be countervailed by a charge derived from the absence of $R^3$ to form an intramolecular salt. Alternatively, it may form a salt with anion species. Examples of anion species include ions of halogens, such as fluorine, chlorine, bromine, and iodine; ions of inorganic acids, such as sulfuric acid, nitric acid, phosphoric acid, perchloric acid, and carbonic acid; ions of carboxylic acids, such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid; ions of amino acids, such as arginine, aspartic acid, and glutamic acid ion; ions of organic acids, such as methanesulfonic acid and p-toluenesulfonic acid.

The cation species represented by $R^{7+}$ is a $C_{1-6}$ alkyl or $C_{2-6}$ alkylene group with a $C_{1-4}$ or $C_{2-4}$ alkylene group being preferred. At least one hydrogen atom on the alkyl and alkylene groups may be substituted. Preferred examples of substituents usable herein include carbamoyl, hydroxyl, amino, and carboxyl groups and halogen atoms, such as fluorine and chlorine.

Preferred are a group of compounds represented by the formula (I) wherein n is 0.

The compounds represented by the formula (I) according to the present invention have (E) and (Z) isomers depending upon the position of the substituent for the substituted vinyl group at the 3-position, and the present invention encompasses the (E) and (Z) isomers or mixtures thereof. Further, isomers attributable to other group(s) in the formula (I) and mixtures thereof are also encompassed in the present invention.

The compounds represented by the formula (I) according to the present invention may be present in the form of a salt. Salts usable herein include pharmaceutically acceptable nontoxic salts. Preferable examples of a salt formed at the amino and/or imidazothiazolium group include salts of hydrohalogenic acids, such as hydrofluoric acid, hydrochloric acid, hydrobromic acid, and hydroiodic acid; salts of inorganic acids, such as sulfuric acid, nitric acid, phosphoric acid, perchloric acid, and carbonic acid; salts of carboxylic acids, such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid; salts of amino acids, such as arginine, aspartic acid, and glutamic acid; and salts of organic acids, such as methanesulfonic acid and p-toluenesulfonic acid. Examples of salts formed at the carboxyl group include alkali metal salts, such as sodium, potassium, and lithium salts; alkaline earth metal salts, such as calcium and magnesium salts; ammonium salts; salts of organic amines, such as triethylamine, trimethylamine, diethylamine, pyridine, ethanolamine, triethanolamine, dicyclohexyl amine, procaine, benzyl amine, N-methylpiperidine, N-methylmorpholine, and diethylaniline; salts of basic amino acids, such as lysine, arginine, and histidine; and salts with organic bases, such as picoline, dicyclohexylamine, and N,N'-dibenzylethylenediamine salts.

The compounds represented by the formula (I) according to the present invention may be provided as metabolically unstable esters which are metabolized in vivo to give the compounds represented by the formula (I). Such metabolically unstable esters include pivaloyloxymethyl, 1-acetoxyethyl, 1-isopropyloxycarbonyloxyethyl, and 1-cyclohexyloxycarbonyloxyethyl.

Specific examples of compounds according to the present invention include:

p-methoxybenzyl (6R,7R)-7-[(Z)-2-methoxyimino-2-(2-tritylaminothiazol-4-yl)acetamido]-3-[2-(imidazo[5,1-b]thiazol-3-yl)vinyl]-3-cephem-4-carboxylate (a mixture of cis and trans isomers);

sodium (6R,7R)-7-[(Z)-2-(2-aminothiazol-4-yl)-2-methoxyiminoacetamido]-3-[2-(imidazo[5,1-b]thiazol-3-yl)vinyl]-3-cephem-4-carboxylate (cis isomer) (trans isomer);

p-methoxybenzyl (6R,7R)-7-[(Z)-2-(2-tritylaminothiazol-4-yl)-2-trityloxyiminoacetamido]-3-[2-(imidazo[5,1-b]thiazol-3-yl)vinyl]-3-cephem-4-carboxylate (a mixture of cis and trans isomers);

sodium (6R,7R)-7-[(Z)-2-(2-aminothiazol-4-yl)-2-hydroxyiminoacetamido]-3-[2-(imidazo[5,1-b]thiazol-3-yl)vinyl]-3-cephem-4-carboxylate (cis isomer) (trans isomer);

p-methoxybenzyl (6R,7R)-7-[(Z)-2-(2-tritylaminothiazol-4-yl)-2-trityloxyiminoacetamido]-3-[2-(6-methylimidazo[5,1-b]thiazolium-3-yl)vinyl]-3-cephem-4-carboxylate iodide (cis isomer);

(6R,7R)-7-[(Z)-2-(2-aminothiazol-4-yl)-2-hydroxyiminoacetamido]-3-[2-(6-methylimidazo[5,1-b]thiazolium-3-yl)vinyl]-3-cephem-4-carboxylate (cis isomer);

p-methoxybenzyl (6R,7R)-7-[(Z)-2-ethoxyimino-2-(2-tritylaminothiazol-4-yl)acetamido]-3-[2-(imidazo[5,1-b]thiazol-3-yl)vinyl]-3-cephem-4-carboxylate (a mixture of cis and trans isomers);

sodium (6R,7R)-7-[(Z)-2-(2-aminothiazol-4-yl)-2-ethoxyiminoacetamido]-3-[2-(imidazo[5,1-b]thiazol-3-yl)vinyl]-3-cephem-4-carboxylate (cis isomer) (trans isomer);

p-methoxybenzyl (6R,7R)-7-[(Z)-2-ethoxyimino-2-(2-tritylaminothiazol-4-yl)acetamido]-3-[2-(6-methylimidazo[5,1-b]thiazolium-3-yl)vinyl]-3-cephem-4-carboxylate iodide (a mixture of cis and trans isomers);

(6R,7R)-7-[(Z)-2-(2-aminothiazol-4-yl)-2-ethoxyiminoacetamido]-3-[2-(6-methylimidazo[5,1-b]thiazolium-3-yl)vinyl]-3-cephem-4-carboxylate (a mixture of cis and trans isomers);

p-methoxybenzyl (6R,7R)-7-[(Z)-2-fluoromethoxyimino-2-(5-tritylamino-1,2,4-thiadiazol-3-yl)acetamido]-3-[2-(imidazo[5,1-b]thiazol-3-yl)vinyl]-3-cephem-4-carboxylate (a mixture of cis and trans isomers);

sodium (6R,7R)-7-[(Z)-2-(5-amino-1,2,4-thiadiazol-3-yl)-2-fluoromethoxyiminoacetamido]-3-[2-(imidazo[5,1-b]thiazol-3-yl)vinyl]-3-cephem-4-carboxylate (cis isomer) (trans isomer);

p-methoxybenzyl (6R,7R)-7-[(Z)-2-fluoromethoxyimino-2-(5-tritylamino-1,2,4-thiadiazol-3-yl)acetamido]-3-[2-(6-methylimidazo[5,1-b]thiazolium-3-yl)vinyl]-3-cephem-4-carboxylate iodide (trans isomer);

(6R,7R)-7-[(Z)-2-(5-amino-1,2,4-thiadiazol-3-yl)-2-fluoromethoxyiminoacetamido]-3-[2-(6-methylimidazo[5,1-b]thiazolium-3-yl)vinyl]-3-cephem-4-carboxylate (trans isomer);

p-methoxybenzyl (6R,7R)-7-[(Z)-2-cyclopentyloxyimino-2-(5-tritylamino-1,2,4-thiadiazol-3-yl)acetamido]-3-[2-(imidazo[5,1-b]thiazol-3-yl)vinyl]-3-cephem-4-carboxylate (a mixture of cis and trans isomers);

sodium (6R,7R)-7-[(Z)-2-(5-amino-1,2,4-thiadiazol-3-yl)-2-cyclopentyloxyiminoacetamido]-3-[2-(imidazo[5,1-b]thiazol-3-yl)vinyl]-3-cephem-4-carboxylate (cis isomer) (trans isomer);

p-methoxybenzyl (6R,7R)-7-[(Z)-2-cyclopentyloxyimino-2-(5-tritylamino-1,2,4-thiadiazol- 3-yl)acetamido]-3-[2-(6-methylimidazo[5,1-b]thiazolium-3-yl)vinyl]-3-cephem-4-carboxylate iodide (trans isomer);

(6R,7R)-7-[(Z)-2-(5-amino-1,2,4-thiadiazol-3-yl)-2-cyclopentyloxyiminoacetamido]-3-[2-(6-methylimidazo[5,1-b]thiazolium-3-yl)vinyl]-3-cephem-4-carboxylate (trans isomer);

p-methoxybenzyl (6R,7R)-7-[(Z)-2-methoxyimino-2-(2-tritylaminothiazol-4-yl)acetamido]-3-[2-(3-methylimidazo[5,1-b]thiazol-2-yl)vinyl]-3-cephem-4-carboxylate (cis isomers);

sodium (6R,7R)-7-[(Z)-2-(2-aminothiazol-4-yl)-2-methoxyiminoacetamido]-3-[2-(3-methylimidazo[5,1-b]thiazol-2-yl)vinyl]-3-cephem-4-carboxylate (cis isomer);

p-methoxybenzyl (6R,7R)-7-[(Z)-2-ethoxyimino-2-(2-tritylaminothiazol-4-yl)acetamido]-3-[2-(3-methylimidazo[5,1-b]thiazol-2-yl)vinyl]-3-cephem-4-carboxylate (a mixture of cis and trans isomers);

sodium (6R,7R)-7-[(Z)-2-(2-aminothiazol-4-yl)-2-ethoxyiminoacetamido]-3-[2-(3-methylimidazo[5,1-b]

thiazol-2-yl)vinyl]-3-cephem-4-carboxylate (a mixture of cis and trans isomers);

p-methoxybenzyl (6R,7R)-7-[(Z)-2-ethoxyimino-2-(2-tritylaminothiazol-4-yl)acetamido]-3-[2-(3,6-dimethylimidazo[5,1-b]thiazolium-2-yl)vinyl]-3-cephem-4-carboxylate iodide (a mixture of cis and trans isomers);

(6R,7R)-7-[(Z)-2-(2-aminothiazol-4-yl)-2-ethoxyiminoacetamido]-3-[2-(3,6-dimethylimidazo[5,1-b]thiazolium-2-yl)vinyl]-3-cephem-4-carboxylate (a mixture of cis and trans isomers);

p-methoxybenzyl (6R,7R)-7-[(Z)-2-fluoromethoxyimino-2-(5-tritylamino-1,2,4-thiadiazol-3-yl)acetamido]-3-[2-(3-methylimidazo[5,1-b]thiazol-2-yl)vinyl]-3-cephem-4-carboxylate (a mixture of cis and trans isomers);

sodium (6R,7R)-7-[(Z)-2-(5-amino-1,2,4-thiadiazol-3-yl)-2-fluoromethoxyiminoacetamido]-3-[2-(3-methylimidazo[5,1-b]thiazol-2-yl)vinyl]-3-cephem-4-carboxylate (cis isomer) (trans isomer);

p-methoxybenzyl (6R,7R)-7-[(Z)-2-fluoromethoxyimino-2-(5-tritylamino-1,2,4-thiadiazol-3-yl)acetamido]-3-[2-(3,6-dimethylimidazo[5,1-b]thiazolium-2-yl)vinyl]-3-cephem-4-carboxylate iodide (cis isomer); and (6R,7R)-7-[(Z)-2-(5-amino-1,2,4-thiadiazol-3-yl)-2-fluoromethoxyiminoacetamido]-3-[2-(3,6-dimethylimidazo[5,1-b]thiazolium-2-yl)vinyl]-3-cephem-4-carboxylate (cis isomer).

Preparation of Compounds

The compounds represented by the general formula (I) according to the present invention can be preferably prepared by the following process (A) or (B).

Process (A)

Preferably, the compounds represented by the formula (I) may be prepared by the following scheme:

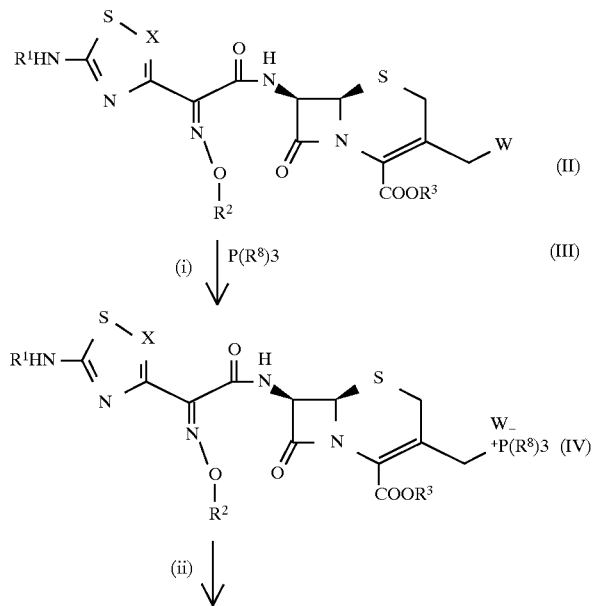

wherein X, $R^1$, $R^2$, $R^3$, $R^4$, $R^5$, $R^6$, and $R^7$ are as defined in the formula (I) above, $R^8$ represents an aryl group, and W represents a halogen.

Each step will now be described in detail.

Step (i)

A trisubstituted phosphine represented by the formula (III) is reacted with a compound represented by the formula (II) or a salt thereof. Suitable salts of the compound represented by the formula (II) include salts with the same bases as exemplified above in connection with the compounds represented by the formula (I).

Preferably, this reaction is carried out in the presence of a metal halide, such as an alkali metal halide, such as sodium iodide, potassium iodide, or sodium bromide. It is carried out in a solvent of acetone, N,N-dimethylformamide, dimethyl sulfoxide, methylene chloride, tetrahydrofuran, ethyl acetate, or a mixture of the above solvents. While the reaction temperature is not particularly limited, in general, it is preferably room temperature. If necessary, the compound represented by the formula (IV) may be isolated.

Step (ii)

A base is allowed to act on the compound represented by the formula (IV) or a salt thereof. Suitable salts of the compound represented by the formula (IV) include salts with the same bases as exemplified above in connection with the compounds represented by the formula (I).

Preferred examples of bases usable in this step include inorganic bases, for example, alkali metal hydrogencarbonates (for example, sodium hydrogencarbonate and potassium hydrogencarbonate), alkali carbonates (for example, sodium carbonate and potassium carbonate), alkaline earth metal carbonates (for example, calcium carbonate), and tri (lower) alkylamines (for example, trimethylamine and triethylamine), pyridine, N-(lower) alkylmorpholine, N-N-di(lower) alkylbenzylamine.

Preferably, the reaction is carried out in a solvent of acetone, tetrahydrofuran, methylene chloride, or water or a mixture of the above solvents. While the reaction temperature is not particularly limited, it is preferably room temperature. If necessary, the compound represented by the formula (V) may be isolated.

Step (iii)

An aldehyde represented by the formula (VI) is then reacted with the compound represented by the formula (V) or a salt thereof. Suitable salts of the compound represented by the formula (V) include salts with the same bases as exemplified above in connection with the compounds represented by the formula (I).

Preferably, the reaction is carried out in a solvent of methylene chloride, tetrahydrofuran, dioxane, or a mixture thereof. While the reaction temperature is not particularly limited, in general, the reaction is preferably carried out under cooling or around room temperature.

The base and the aldehyde may be simultaneously allowed to act on the compound represented by the formula (IV) without successively conducting the steps (ii) and (iii).

Step (iv)

This step is carried out in order to add $R^7$. Therefore, when compounds represented by the formula (I) wherein $R^7$ is absent is desired, the step (iv) may be omitted.

An alkyl halide represented by the formula (VII) is reacted with the compound represented by the formula (VI) or a salt thereof. Suitable salts of the compound represented by the formula (VI) include salts with the bases as described above in connection with the formula (I).

Preferably, this reaction is carried out in a solvent of methylene chloride, tetrahydrofuran, dioxane, or a mixture thereof. While the reaction temperature is not particularly limited, in general, the reaction is preferably carried out under cooling or around room temperature.

Process (B)

The compounds represented by the formula (I) may be prepared by the following scheme:

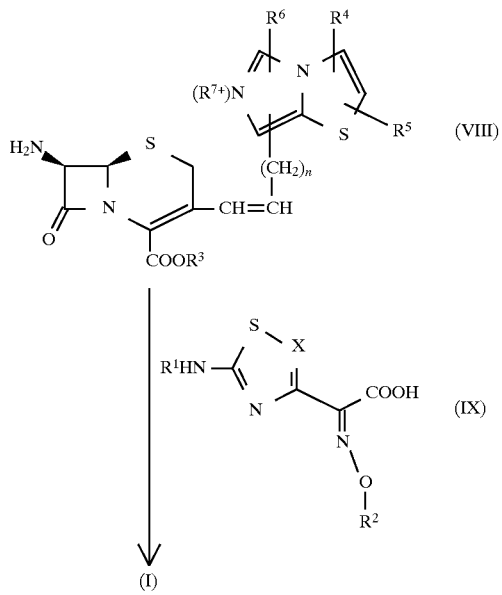

wherein X, $R^1$, $R^2$, $R^3$, $R^4$, $R^5$, $R^6$, and $R^7$ are defined above in the formula (I) above and W represents a halogen.

In this process, the compounds represented by the formula (I) may be prepared by reacting a compound represented by the formula (VIII), a reactive derivative thereof formed at the amino group, or a salt thereof with a compound represented by the formula (IX), a reactive derivative thereof at the carboxyl group, or a salt thereof. The reaction may be carried out in a solvent, such as water, acetone, dioxane, acetonitrile, chloroform, methylene chloride, tetrahydrofuran, ethyl acetate, N,N-dimethylformamide, or pyridine, or other organic solvents inert to the reaction. These solvents may be used as a mixture thereof with water.

Preferred examples of reactive derivatives, formed at the amino group, of the compound represented by the formula (VIII) include Schiff base imino or enamine isomer, which is a tautomer thereof, prepared by reacting the compound represented by the formula (VIII) with a carbonyl compound, such as an aldehyde or a ketone. Further examples thereof include a derivative prepared by reacting the compound of the formula (VIII) with a silyl derivative, such as bis(trimethylsilyl)acetamide, or by reacting the compound of the formula (VIII) with phosphorus trichloride or phosgene.

Suitable salts of the compounds represented by the formulae (VIII) and (IX) include acid addition salts, such as salts with organic acids (for example, salts with acetic acid, maleic acid, tartaric acid, benzenesulfonic acid, and toluenesulfonic acid) and salts with inorganic acids (for example, salts with hydrochloric acid, hydrobromic acid, sulfuric acid, and phosphoric acid); metal salts, such as alkali metal or alkaline earth metal salts (for example, sodium, potassium, calcium, and magnesium salts); ammonium salts; and organic amines (for example, triethylamine and dicyclohexylamine salts).

Examples of suitable reactive derivatives, formed at the carboxy group, of the compound represented by the formula (IX) include acid halides, acid azides, acid anhydrides, activated amides, and activated esters. More specific examples thereof include: acid chlorides; acid bromides; mixed acid anhydrides with acids, such as substituted phosphoric acids (for example, dialkylphosphoric acids, dibenzylphosphoric acid, and halogenated phosphoric acids), dialkylphosphorous acids, sulfurous acid, thiosulfuric acid, sulfuric acid, alkyl carbonates (for example, methyl carbonate and ethyl carbonate), aliphatic carbonic acids (for example, pivalic acid, valeric acid, isovaleric acid, and trichloroacetic acid), or aromatic carboxylic acids (for example, benzoic acid); activated amides with imidazole, dimethylpyrazole, triazole, or tetrazole; activated esters (for example, cyanomethyl ester, methoxymethyl ester, dimethyliminomethyl [$(CH_3)_2N=CH-$] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, and 8-quinolyl thioester); and N-hydroxy compounds (for example, N,N-dimethylhydroxylamine, 1-hydroxy-2-(1H)-pyridone, N-hydroxysccinimide, N-hydroxyphthalimide, and 1-hydroxy-6-chloro-1H-benzotriazole). These reactive derivatives may be suitably selected according to the compound of the formula (IX) as a reactant.

In the above reaction, when the compound of the formula (VIII) is used in a free form or a salt form, condensing agents usable herein include, for example, N,N'-dicyclohexylcarbodiimide, N-cyclohexyl-N'-morpholinocarbodiimide, N-cyclohexyl-N'-(4-diethylaminocyclohexyl)carbodiimide, N-N'-diethylcarbodiimide, N,N'-diisopropylcarbodiimide, N-ethyl-N'-(3-dimethylaminopropyl)carbodiimide, N,N-carbonylbis(2-methylimidazole), pentamethyleneketene-N-cyclohexylimine diphenylketene-N-cyclohexylimine, ethoxyacetylene, 1-alkoxy-1-chloroethylene, trialkyl phosphite, ethyl polyphosphate, isopropyl polyphosphate, phosphorus oxychloride, phosphorus trichloride, thionyl chloride, triphenylphosphine, 2-ethyl-5-(m-sulfophenyl) isoxazolium hydroxide intramolecular salt, 1-(p-chlorobenzenesulfonyloxy)-6-chloro-1H-benztriazole, and a Vilsmeyer's reagent prepared by reacting dimethylformamide with thionyl chloride, phosgene, phosphorus oxychloride or the like.

This reaction may also be carried out in the presence of an inorganic or organic base. Bases usable herein include inorganic bases, such as alkali metal hydrogencarbonates (for example, sodium hydrogencarbonate and potassium hydrogencarbonate), alkaline earth metal carbonates (such as calcium carbonate), and organic bases, such as tri (lower) alkylamine (for example, trimethylamine and triethylamine), pyridine, N— (lower) alkylmorpholine, and N,N-di (lower) alkylbenzylamine. The reaction temperature is not particularly limited. In general, however, the reaction is preferably carried out under cooling or heating.

If necessary, the hydroxy protective group and/or the carboxyl protective group and/or amino protective group may be removed from the compound (I) of the present invention prepared by the above reaction. Further, if necessary, the carboxyl group may be converted to a metabolically unstable nontoxic ester group. The carboxyl protective group and/or the amino protective group may be removed by any method which is suitably selected according to the protective group to be removed. For example, the amino protective group may be removed by hydrolysis or reduction, and, in the case of the compound having an acyl group as the protective group, the protective group may be removed by any conventional method, such as a method wherein the compound is reacted with an imino halogenating agent and then with an imino etherifying agent, if necessary, followed by hydrolysis. Hydrolysis using an acid is one of the commonly used methods and may be applied to the removal of groups, for example, alkoxycarbonyl, formyl, and trityl groups. Formic acid, trifuloroacetic acid, hydrochloric acid and the like may be suitably selected according to the type of the amino group. The reaction may be carried out in the absence of a solvent or in the presence of water, a hydrophilic organic solvent, or a mixture of the above solvents. When trifluoroacetic acid is used, the reaction may be carried out in the presence of anisole. Any method, such as hydrolysis and reduction, may be applied to the reaction for removing the carboxyl protective group. Further, the hydrolysis, using an acid, which is one of the commonly used methods may be applied to the removal of groups, for example, silyl and diphenylmethyl groups. The conversion to a metabolically unstable ester may be performed by any common method known per se, for example, a reaction of the carboxylic acid with a metal salt and a corresponding alkyl halide, such as a pivaloyloxymethyl halide, or the like in a solvent.

Use of the Compounds/Pharmaceutical Compositions

The compounds according to the present invention have potent antibacterial activity effective against a wide variety of Gram-positive and Gram-negative bacteria. In particular, they have very potent antibacterial activity against *Staphylococcus aureus* (MSSA and MRSA) and Enterococcus (faecalis). Therefore, the compounds according to the present invention can be used for the treatment of infectious diseases in animals including humans, caused by various pathogenic fungi.

A pharmaceutical composition comprising as an active ingredient a compound of the present invention or a pharmaceutically acceptable salt thereof can be administered either orally or parenterally (e.g. intravenous injection, intramuscular injection, subcutaneous administration, rectal administration, or percutaneous administration) to humans or animals other than humans. The pharmaceutical composition comprising as an active ingredient a compound of the present invention may be made into a preparation suitable for an administration route to be adopted. Specifically, it may be made into any of the following preparations: an injection for intravenous or intramuscular injection; a capsule, a tablet, a granule, a powder, a pill, a subtilized granule or a troche for oral administration; a parenteral preparation; and an oily suppository. The above-described various preparations can be prepared by a conventional method using an excipient, a filler, a binder, a wetting agent, a disintegrating agent, a surface active agent, a lubricant, a dispersing agent, a buffer, a preservative, a solubilizer, an antiseptic, a flavor, a soothing agent, a stabilizer and the like. Examples of the above additives which are nontoxic and employable in the preparations include milk sugar, fruit sugar, grape sugar, starch, gelatin, magnesium carbonate, synthetic magnesium silicate, talc, magnesium stearate, methyl cellulose, or a salt thereof, gum arabic, polyethylene glycol, syrup, vaseline, glycerol, ethanol, propylene glycol, citric acid, sodium chloride, sodium sulfite and sodium phosphate.

The dosage of the compound of the present invention is properly determined in consideration of the regimen, the age and sex of a patient, and the conditions of diseases. However, for the treatment of infectious diseases, approximately 100 mg to 4000 mg, preferably 500 mg to 2000 mg of the compound is generally administered per day per adult individual at one time or several times.

EXAMPLES

The present invention will now be described with reference to the following examples.

Preparation 1

Imidazo[5,1-b]thiazole-3-carbaldehyde

In 20 ml of dichloromethane was suspended 0.211 g of 3-hydroxymethylimidazo[5,1-b]thiazole. Manganese dioxide (1.1 g) was added to the suspension, and the mixture was stirred at room temperature for 16 hr. The reaction mixture was filtered, and the filtrate was evaporated to dryness under reduced pressure to give 0.146 g (yield 71%) of the title compound.

NMR (CDCl$_3$): δ 7.11 (1H, s), 7.42 (1H, s), 8.16 (1H, s), 8.66 (1H, s)

Preparation 2

3-Methylimidazo[5,1-b]thiazole-2-carbaldehyde

The procedure of Preparation 1 was repeated, except that 0.554 g of 2-hydroxymethyl-3-methylimidazo[5,1-b]thiazole was used as the starting compound. Thus, 0.468 g (yield 83%) of the title compound was obtained.

NMR (CDCl$_3$): δ 2.78 (3H, s), 7.13 (1H, s), 7.43 (1H, s), 8.15 (1H, s), 8.69 (1H, s)

Example 1 p-Methoxybenzyl (6R,7R)-7-[(Z)-2-methoxyimino-2-(2-tritylaminothiazol-4-yl)acetamido]-3-[2-(imidazo[5,1-b]thiazol-3-yl)vinyl]-3-cephem-4-carboxylate (1:3 mixture of cis and trans isomers)

Sodium iodide (50 mg) was added at room temperature to a solution of 240 mg of p-methoxybenzyl (6R,7R)-7-[(Z)-2-methoxyimino-2-(2-tritylaminothiazol-4-yl)acetamido]-3-chloromethyl-3-cephem-4-carboxylate and 87 mg of triphenylphosphine in 5 ml of acetone, and the mixture was stirred for 1.5 hr. The reaction mixture was evaporated to dryness under reduced pressure, and 10 ml of methylene 2chloride was added thereto. Imidazo[5,1-b]thiazole-3-carbaldehyde (138 mg) was added, and 15 ml of a 5% aqueous sodium hydrogencarbonate solution was added thereto. The mixture was stirred at room temperature for 4 hr and then separated, and the aqueous layer was extracted with methylene chloride. The extract was combined with the organic layer, and the combined extract and organic layer were washed with a saturated saline solution, dried over anhydrous magnesium sulfate, and concentrated under reduced pressure. The concentrate was purified by Sephadex LH 20 column chromatography (eluent: chloroform:methanol=1:1) to give 218 mg (yield 81%) of the title compound.

NMR (CDCl$_3$): δ 3.04 (1/4H, d, J=18 Hz), 3.43 (1/4H, d, J=18 Hz), 3.54 (3/4H, d, J=18 Hz), 3.63 (3/4H, d, J=18 Hz), 3.79 (3/4H, s), 3.81 (9/4H, s), 4.07 (3H, s), 5.22 (1/2H, s), 5.25 (3/2H, s), 7.22 (1H, s), 7.25 (1/4H, s), 7.33 (3/4H, s), 8.53 (3/4H, s), 8.80(1/4H, s)

Example 2

Sodium (6R,7R)-7-[(Z)-2-(2-aminothiazol-4-yl)-2-methoxyiminoacetamido]-3-[2-(imidazo[5,1-b]thiazol-3-yl)vinyl]-3-cephem-4-carboxylate (cis isomer) (trans isomer)

Trifluoroacetic acid (2.5 ml) was added dropwise to a solution of 218 mg of p-methoxybenzyl (6R,7R)-7-[(Z)-2-methoxyimino-2-(2-tritylaminothiazol-4-yl)acetamido]-3-[2-(imidazo[5,1-b]thiazol-3-yl)vinyl]-3-cephem-4-carboxylate (a 1:3 mixture of cis and trans isomers) in 1 ml of anisole under ice cooling. The mixture was stirred under ice cooling for one hr, and cold isopropyl ether was added thereto. The resultant precipitate was collected by filtration, washed with isopropyl ether, dried, and neutralized with a 5% aqueous sodium hydrogencarbonate solution. Thereafter, separation and purification were performed by column chromatography on Diaion HP 20 and Sephadex LH 20 in sequence to give the title compound [cis isomer 23.1 mg (yield 18%) and trans isomer 58.3 mg (yield 45%)].

NMR (D$_2$O)(cis form) δ 3.35 (1H, d, J=18 Hz), 3.59 (1H, d, J=18 Hz), 3.96 (3H, s), 5.26 (1H, d, J=4 Hz), 5.78 (1H, d, J=4 Hz), 6.48 (1H, d, J=12 Hz), 6.72 (1H, d, J=12 Hz), 6.98 (1H, s), 7.23 (1H, s), 7.41 (1H, s), 8.79 (1H, s), (trans form) δ 3.68 (1H, d, J=18 Hz), 3.79 (1H, d, J=18 Hz), 3.98 (3H, s), 5.30 (1H, d, J=4 Hz), 5.82 (1H, d, J=4 Hz), 6.66 (1H, d, J=17 Hz), 7.00 (1H, s), 7.21 (1H, s), 7.22 (1H, s), 7.30 (1H, d, J=17 Hz), 8.55 (1H, s)

Example 3 p-Methoxybenzyl (6R,7R)-7-[(Z)-2-(2-tritylaminothiazol-4-yl)-2-trityloxyiminoacetamido]-3-[2-(imidazo[5,1-b]thiazol-3-yl)vinyl]-3-cephem-4-carboxylate (1:3 mixture of cis and trans isomers)

The procedure of Example 1 was repeated, except that 308 mg of p-methoxybenzyl (6R,7R)-7-[(Z)-2-(2-tritylaminothiazol-4-yl)-2-trityloxyiminoacetamido]-3-chloromethyl-3-cephem-4-carboxylate was used as the starting compound. Thus, 272 mg (yield 80%) of the title compound was obtained.

NMR (CDCl$_3$) δ 3.06 (1/4H, d, J=18 Hz), 3.42 (1/4H, d, J=18 Hz), 3.53 (3/4H, d, J=18 Hz), 3.66 (3/4H, d, J=18 Hz), 3.82 (3H, s), 5.24 (2H, s), 7.22 (1H, s), 7.25 (1/4H, s), 7.35 (3/4H, s), 8.55 (3/4H, s), 8.82 (1/4H, s)

Example 4

Sodium (6R,7R)-7-[(Z)-2-(2-aminothiazol-4-yl)-2-hydroxyiminoacetamido]-3-[2-(imidazo[5,1-b]thiazol-3-yl)vinyl]-3-cephem-4-carboxylate (cis isomer) (trans isomer)

Trifluoroacetic acid (2.5 ml) was added dropwise to a solution of 272 mg of p-methoxybenzyl (6R,7R)-7-[(Z)-2-(2-tritylaminothiazol-4-yl)-2-trityloxyiminoacetamido]-3-[2-(imidazo[5,1-b]thiazol-3-yl)vinyl]-3-cephem-4-carboxylate (a 1:3 mixture of cis and trans isomers) and 500 mg of p-methoxyphenol in 0.5 ml of anisole under ice cooling. The mixture was stirred under ice cooling for one hr, and cold isopropyl ether was added thereto. The resultant precipitate was collected by filtration, washed with isopropyl ether, dried, and neutralized with a 5% aqueous sodium hydrogencarbonate solution. Thereafter, the reaction mixture was purified by column chromatography on Diaion HP 20 and Sephadex LH 20 in sequence to give the title compound [cis isomer 11.2 mg (yield 10%) and trans isomer 30.2 mg (yield 24%)].

NMR (D$_2$O) (cis form) δ 3.33 (1H, d, J=17 Hz), 3.55 (1H, d, J=17 Hz), 5.27 (1H, d, J=5 Hz), 5.83 (1H, d, J=5 Hz), 6.49 (1H, d, J=11 Hz), 6.72 (1H, d, J=11 Hz), 6.96 (1H, s), 7.04 (1H, s), 7.16 (1H, s), 8.80 (1H, s), (trans form) δ 3.75 (1H, d, J=18 Hz), 3.85 (1H, d, J=18 Hz), 5.35 (1H, d, J=5 Hz), 5.90 (1H, d, J=5 Hz), 6.76 (1H, d, J=17 Hz), 7.02 (1H, s), 7.16 (1H, s), 7.19 (1H, s), 7.37 (1H, d, J=17 Hz), 8.55 (1H, s)

Example 5 p-Methoxybenzyl (6R,7R)-7-[(Z)-2-(2-tritylaminothiazol-4-yl)-2-trityloxyiminoacetamido]-3-[2-(6-methylimidazo[5,1-b]thiazolium-3-yl)vinyl]-3-cephem-4-carboxylate iodide (cis isomer)

p-Methoxybenzyl (6R,7R)-7-[(Z)-2-(2-tritylaminothiazol-4-yl)-2-trityloxyiminoacetamido]-3-[2-(imidazo[5,1-b]thiazol-3-yl)vinyl-3-cephem-4-carboxylate (cis isomer) (98.4 mg) was dissolved in 3 mg of methylene chloride. Methyl iodide (1.5 ml) was added to the solution, and the mixture was allowed to react at room temperature for 16 hr. The reaction mixture was evaporated to dryness under reduced pressure. The concentrate was purified by Sephadex LH 20 column chromatography (eluent: chloroform:methanol=1:1) to give 81.2 mg (yield 73%) of the title compound.

NMR (CDCl$_3$) δ 3.07 (1H, d, J=18 Hz), 3.42 (1H, d, J=18 Hz), 4.10 (3H, s), 4.24 (3H, s), 5.22 (2H, s), 7.32 (1H, s), 7.35 (1H, s), 9.55 (3/4H, s)

Example 6

(6R,7R)-7-[(Z)-2-(2-aminothiazol-4-yl)-2-hydroxyiminoacetamido]-3-[2-(6-methylimidazo[5,1-b]thiazolium-3-yl)vinyl]-3-cephem-4-carboxylate (cis isomer)

The procedure of Example 4 was repeated, except that 81.2 mg of p-methoxybenzyl (6R,7R)-7-[(Z)-2-(2-tritylaminothiazol-4-yl)-2-trityloxyiminoacetamido]-3-[2-(6-methylimidazo[5,1-b]thiazolium-3-yl)vinyl]-3-cephem-4-carboxylate iodide (cis isomer) was used as the starting compound. Thus, 18.1 mg (yield 51%) of the title compound was obtained.

NMR (D$_2$O) δ 3.36 (1H, d, J=17 Hz), 3.62 (1H, d, J=17 Hz), 4.08 (3H, s), 5.29 (1H, d, J=5 Hz), 5.82 (1H, d, J=5 Hz), 6.46 (1H, d, J=11 Hz), 6.75 (1H, d, J=11 Hz), 6.79 (1H, s), 7.36 (1H, s), 7.62 (1H, s), 9.20 (1H, s)

Example 7 p-Methoxybenzyl (6R,7R)-7-[(Z)-2-ethoxyimino-2-(2-tritylaminothiazol-4-yl)acetamido]-3-[2-(imidazo[5,1-b]thiazol-3-yl)vinyl]-3-cephem-4-carboxylate (1:3 mixture of cis and trans isomers)

The procedure of Example 1 was repeated, except that 243 mg of p-methoxybenzyl (6R,7R)-7-[(Z)-2-ethoxyimino- 2-(2-tritylaminothiazol-4-yl)acetamido]-3-chloromethyl-3-cephem-4-carboxylate was used as the starting compound. Thus, 216 mg (yield 76%) of the title compound was obtained.

NMR (CDCl$_3$) δ 1.33 (3/4H, t, J=7 Hz), 1.36 (1/4H, t, 7 Hz), 3.07 (1/4H, d, J=18 Hz), 3.40 (1/4H, d, J=18 Hz), 3.54 (3/4H, d, J=18 Hz), 3.67 (3/4H, d, J=18 Hz), 4.07 (3H, s), 4.26 (2H, q, J=7 Hz), 5.24 (1/2H, s), 5.27 (3/2H, s), 7.24 (1H, s), 7.23 (1/4H, s), 7.37 (3/4H, s), 8.58 (3/4H, s), 8.81 (1/4H, s)

Example 8

Sodium (6R,7R)-7-[(Z)-2-(2-aminothiazol-4-yl)-2-ethoxyiminoacetamido]-3-[2-(imidazo[5,1-b]thiazol-3-yl)vinyl]-3-cephem-4-carboxylate (cis isomer) (trans isomer)

The procedure of Example 2 was repeated, except that 216 mg of p-methoxybenzyl (6R,7R)-7-[(Z)-2-ethoxyimino-2-(2-tritylaminothiazol-4-yl)acetamido]-3-[2-(imidazo[5,1-b]thiazol-3-yl)vinyl]-3-cephem-4-carboxylate (a 1:3 mixture of cis and trans isomers) was used as the starting compound. Thus, the title compound [cis isomer: 20.0 mg (yield 15%), trans isomer: 62.6 mg (yield 48%)] was obtained.

NMR (D$_2$O) (cis form) δ 1.31 (3H, t, J=6 Hz), 3.36 (1H, d, J=18 Hz), 3.60 (1H, d, J=18 Hz), 4.27 (2H, q, J=6 Hz), 5.29 (1H, d, J=5 Hz), 5.81 (1H, d, J=5 Hz), 6.52 (1H, d, J=12 Hz), 6.76 (1H, d, J=12 Hz), 7.00 (1H, s), 7.22 (1H, s), 7.38 (1H, s), 8.81 (1H, s), (trans form) δ 1.35 (3H, t, J=6 Hz), 3.74 (1H, d, J=18 Hz), 3.85 (1H, d, J=18 Hz), 4.29 (2H, q, J=6 Hz), 5.34 (1H, d, J=5 Hz), 5.86 (1H, d, J=5 Hz), 6.73 (1H, d, J=15 Hz), 7.02 (1H, s), 7.27 (2H, s), 7.36 (1H, d, J=15 Hz), 8.63 (1H, s)

Example 9 p-Methoxybenzyl (6R,7R)-7-[(Z)-2-ethoxyimino-2-(2-tritylaminothiazol-4-yl)acetamido]-3-[2-(6-methylimidazo[5,1-b]thiazolium-3-yl)vinyl]-3-cephem-4-carboxylate iodide (1:3 mixture of cis and trans isomers)

The procedure of Example 5 was repeated, except that 250 mg of p-methoxybenzyl (6R,7R)-7-[(Z)-2-ethoxyimino-2-(2-tritylaminothiazol-4-yl)acetamido]-3-[2-(imidazo[5,1-b]thiazol-3-yl)vinyl-3-cephem-4-carboxylate (a 1:3 mixture of cis and trans isomers) was used as the starting compound. Thus, 255 mg (yield 88%) of the title compound was obtained.

NMR (CDCl$_3$) δ 1.33 (3/4H, t, J=7 Hz), 1.36 (1/4H, t, J=7 Hz), 3.07 (1/4H, d, J=18 Hz), 3.39 (1/4H, d, J=18 Hz), 3.57 (3/4H, d, J=18 Hz), 3.67 (3/4H, d, J=18 Hz), 4.07 (3H, s), 4.11 (3H, s), 4.28 (2H, q, J=7 Hz), 5.22 (1/2H, s), 5.25 (3/2H, s), 7.24 (1H, s), 7.34 (1/4H, s), 7.44 (3/4H, s), 9.27 (3/4H, s), 9.46 (1/4H, s)

Example 10

(6R,7R)-7-[(Z)-2-(2-Aminothiazol-4-yl)-2-ethoxyiminoacetamido]-3-[2-(6-methylimidazo[5,1-b]thiazolium-3-yl)vinyl]-3-cephem-4-carboxylate (1:3 mixture of cis and trans isomers)

The procedure of Example 2 was repeated, except that 255 mg of p-methoxybenzyl (6R,7R)-7-[(Z)-2-ethoxyimino-2-(2-tritylaminothiazol-4-yl)acetamido]-3-[2-(6-methylimidazo[5,1-b]thiazolium-3-yl)vinyl]-3-cephem-4-carboxylate iodide (a 1:3 mixture of cis and trans isomers) was used as the starting compound. Thus, 101 mg (yield 66%) of the title compound was obtained.

NMR (D$_2$O) δ 1.29 (9/4H, t, J=7 Hz), 1.32 (3/4H, t, J=7 Hz), 3.36 (3/4H, d, J=18 Hz), 3.62 (3/4H, d, J=18 Hz), 3.76 (1/4H, d, J=18 Hz), 3.85 (1/4H, d, J=18 Hz), 4.08 (9/4H, s), 4.12 (3/4H, s), 4.27 (1/2H, q, J=7 Hz), 4.30 (3/2H, q, J=7 Hz), 5.28 (3/4H, d, J=4 Hz), 5.32 (1/4H, d, J=4 Hz), 5.78 (3/4H, d, J=4 Hz), 5.84 (1/4H, d, J=4 Hz), 6.45 (1/4H, d, J=12 Hz), 6.74 (1/4H, d, J=12 Hz), 6.77 (3/4H, d, J=16 Hz), 6.79 (3/4H, s), 6.98 (1/4H, s), 7.35 (3/4H, d, J=16 Hz), 7.36 (1/4H, s), 7.52 (3/4H, s), 7.62 (1/4H, s), 7.65 (3/4H, s), 9.20 (1/4H, s), 9.34 (3/4H, s)

Example 11 p-Methoxybenzyl (6R,7R)-7-[(Z)-2-fluoromethoxyimino-2-(5-tritylamino-1,2,4-thiadiazol-3-yl)acetamido]-3-[2-(imidazo[5,1-b]thiazol-3-yl)vinyl]-3-cephem-4-carboxylate (trans isomer)

The procedure of Example 1 was repeated, except that 480 mg of p-methoxybenzyl (6R,7R)-7-r(Z)-2-fluoromethoxyimino-2-(5-tritylamino-1,2,4-thiadiazol-3-yl) acetamido]-3-chloromethyl-3-cephem-4-carboxylate was used as the starting compound. Thus, 298 mg (yield 55%) of the title compound was obtained.

NMR (CDCl$_3$) δ 3.77 (1H, d, J=18 Hz), 3.89 (1H, d, J=18 Hz), 4.11 (3H, s), 5.25 (2H, s), 5.88 (1H, d, J=5 Hz), 6.70 (1H, d, J=15 Hz), 7.09 (2H, s), 7.33 (1H, d, J=15 Hz), 8.36 (1H, s)

Example 12

Sodium (6R,7R)-7-[(Z)-2-(5-amino-1,2,4-thiadiazol-3-yl)-2-fluoromethoxyiminoacetamido]-3-[2-(imidazo[5,1-b]thiazol-3-yl)vinyl]-3-cephem-4-carboxylate (trans isomer)

The procedure of Example 2 was repeated, except that 198 mg of p-methoxybenzyl (6R,7R)-7-[(Z)-2-fluoromethoxyimino-2-(5-tritylamino-1,2,4-thiadiazol-3-yl) acetamido]-3-[2-(imidazo[5,1-b]thiazol-3-yl)vinyl]-3-cephem-4-carboxylate (trans isomer) was used as the starting compound. Thus, 41.5 mg (yield 35%) of the title compound was obtained.

NMR (D$_2$O) δ 3.75 (1H, d, J=18 Hz), 3.86 (1H, d, J=18 Hz), 5.31 (1H, d, J=5 Hz), 5.85 (2H, d, J=56 Hz), 5.88 (1H, d, J=5 Hz), 6.67 (1H, d, J=15 Hz), 7.08 (1H, s), 7.11 (1H, s), 7.31 (1H, d, J=15 Hz), 8.34 (1H, s)

Example 13 p-Methoxybenzyl (6R,7R)-7-[(Z)-2-fluoromethoxyimino-2-(5-tritylamino-1,2,4-thiadiazol-3-yl)acetamido]-3-[2-(6-methylimidazo[5,1-b]thiazolium-3-yl)vinyl]-3-cephem- 4-carboxylate iodide (trans isomer)

The procedure of Example 5 was repeated, except that 100 mg of p-methoxybenzyl (6R,7R)-7-[(Z)-2-fluoromethoxyimino-2-(5-tritylamino-1,2,4-thiadiazol-3-yl) acetamido]-3-[2-(imidazo[5,1-b]thiazol-3-yl)vinyl]-3-cephem-4-carboxylate (trans isomer) was used as the starting compound. Thus, 94.6 mg (yield 83%) of the title compound was obtained.

NMR (CDCl$_3$) δ 3.76 (1H, d, J=18 Hz), 3.89 (1H, d, J=18 Hz), 4.10 (6H, s), 5.25 (2H, s), 6.70 (1H, d, J=15 Hz), 7.38 (1H, d, J=15 Hz), 7.55 (1H, s), 9.29 (1H, s)

Example 14

(6R,7R)-7-[(Z)-2-(5-Amino-1,2,4-thiadiazol-3-yl)-2-fluoromethoxyiminoacetamido]-3-[2-(6-methylimidazo[5,1-b]thiazolium-3-yl)vinyl]-3-cephem-4-carboxylate (trans isomer)

The procedure of Example 2 was repeated, except that 94.6 mg of p-methoxybenzyl (6R,7R)-7-[(Z)-2-fluoromethoxyimino-2-(5-tritylamino-1,2,4-thiadiazol-3-yl)acetamido]-3-[2-(6-methylimidazo[5,1-b]thiazolium-3-yl)vinyl]-3-cephem-4-carboxylate iodide (trans isomer) was used as the starting compound. Thus, 27.5 mg (yield 56%) of the title compound was obtained.

NMR ($D_2O$) δ 3.74 (1H, d, J=18 Hz), 3.84 (1H, d, J=18 Hz), 4.12 (3H, s), 5.33 (1H, d, J=5 Hz), 5.86 (2H, d, J=54 Hz), 5.87 (1H, d, J=5 Hz), 6.76 (1H, d, J=15 Hz), 7.35 (1H, d, J=15 Hz), 7.52 (1H, s), 7.65 (1H, s), 9.31 (1H, s)

Example 15 p-Methoxybenzyl (6R,7R)-7-[(Z)-2-cyclopentyloxyimino-2-(5-tritylamino-1,2,4-thiadiazol-3-yl)acetamido]-3-[2-(imidazo[5,1-b]thiazol-3-yl)vinyl]-3-cephem-4-carboxylate (1:3 mixture of cis and trans isomers)

The procedure of Example 1 was repeated, except that 497 mg of p-methoxybenzyl (6R,7R)-7-[(Z)-2-cyclopentyloxyimino-2-(5-tritylamino-1,2,4-thiadiazol-3-yl)acetamido]-3-chloromethyl-3-cephem-4-carboxylate was used as the starting compound. Thus, 505 mg (yield 91%) of the title compound was obtained.

NMR ($CDCl_3$) δ 1.55–2.10 (8H, m), 3.09 (1/4H, d, J=18 Hz), 3.39 (1/4H, d, J=18 Hz), 3.58 (3/4H, d, J=18 Hz), 3.66 (3/4H, d, J=18 Hz), 4.08 (3H, s), 5.23 (2H, s), 7.04 (1H, s), 7.10 (1/4H, s), 7.17 (3/4H, s), 7.44 (3/4H, s), 7.46 (1/4H, s)

Example 16

Sodium (6R,7R)-7-[(Z)-2-(5-amino-1,2,4-thiadiazol-3-yl)-2-cyclopentyloxyiminoacetamido]-3-[2-(imidazo[5,1-b]thiazol-3-yl)vinyl]-3-cephem-4-carboxylate (cis isomer) (trans isomer)

The procedure of Example 2 was repeated, except that 243 mg of p-methoxybenzyl (6R,7R)-7-[(Z)-2-cyclopentyloxyimino-2-(5-tritylamino-1,2,4-thiadiazol-3-yl)acetamido]-3-[2-(imidazo[5,1-b]thiazol-3-yl)vinyl]-3-cephem-4-carboxylate (a mixture of cis and trans isomers) was used as the starting compound. Thus, the title compound [cis isomer: 23.5 mg (yield 16%), trans isomer: 69.1 mg (yield 46%)] was obtained.

NMR ($D_2O$) (cis form) δ 1.55–2.10 (8H, m), 3.40 (1H, d, J=18 Hz), 3.63 (1H, d, J=18 Hz), 5.26 (1H, d, J=5 Hz), 5.86 (1H, d, J=5 Hz), 6.48 (1H, d, J=11 Hz), 6.69 (1H, d, J=11 Hz), 7.06 (1H, s), 7.16 (1H, s), 7.36 (1H, s) (trans form) δ 1.55–2.10 (8H, m), 3.69 (1H, d, J=18 Hz), 3.82 (1H, d, J=18 Hz), 5.32 (1H, d, J=5 Hz), 5.84 (1H, d, J=5 Hz), 6.69 (1H, d, J=15 Hz), 7.10 (1H, s), 7.14 (1H, s), 7.35 (1H, d, J=15 Hz)

Example 17 p-Methoxybenzyl (6R,7R)-7-[(Z)-2-cyclopentyloxyimino-2-(5-tritylamino-1,2,4-thiadiazol-3-yl)acetamido]-3-[2-(6-methylimidazo[5,1-b]thiazolium-3-yl)vinyl]-3-cephem-4-carboxylate iodide (trans isomer)

The procedure of Example 5 was repeated, except that 94.6 mg of p-methoxybenzyl (6R,7R)-7-[(Z)-2-cyclopentyloxyimino-2-(5-tritylamino-1,2,4-thiadiazol-3-yl)acetamido]-3-[2-(imidazo[5,1-b]thiazol-3-yl)vinyl]-3-cephem-4-carboxylate (trans isomer) was used as the starting compound. Thus, 93.4 mg (yield 86%) of the title compound was obtained.

NMR ($CDCl_3$) δ 1.55–2.10 (8H, m), 3.58 (1H, d, J=18 Hz), 3.66 (1H, d, J=18 Hz), 4.08 (3H, s), 4.12 (3H, s), 5.23 (2H, s), 6.82 (1H, d, J=15 Hz), 7.10 (1H, d, J=15 Hz), 7.44 (1H, s), 7.66 (1H, s), 8.33 (1H, s)

Example 18

(6R,7R)-7-[(Z)-2-(5-amino-1,2,4-thiadiazol-3-yl)-2-cyclopentyloxyiminoacetamido]-3-[2-(6-methylimidazo[5,1-b]thiazolium-3-yl)vinyl]-3-cephem-4-carboxylate (trans isomer)

The procedure of Example 2 was repeated, except that 94.6 mg of p-methoxybenzyl (6R,7R)-7-[(Z)-2-cyclopentyloxyimino-2-(5-tritylamino-1,2,4-thiadiazol-3-yl)acetamido]-3-[2-(6-methylimidazo[5,1-b]thiazolium-3-yl)vinyl]-3-cephem-4-carboxylate iodide (trans isomer) was used as the starting compound. Thus, 42.2 mg (yield 81%) of the title compound was obtained.

NMR ($D_2O$) δ 1.55–2.10 (8H, m), 3.70 (1H, d, J=18 Hz), 3.81 (1H, d, J=18 Hz), 4.10 (3H, s), 5.35 (1H, d, J=5 Hz), 5.85 (1H, d, J=5 Hz), 6.81 (1H, d, J=15 Hz), 7.12 (1H, d, J=15 Hz), 7.55 (1H, s), 7.68 (1H, s), 8.35 (1H, s)

Example 19 p-Methoxybenzyl (6R,7R)-7-[(Z)-2-methoxyimino-2-(2-tritylaminothiazol-4-yl)acetamido]-3-[2-(3-methylimidazo[5,1-b]thiazol-2-yl)vinyl]-3-cephem-4-carboxylate (cis isomers)

Sodium iodide (50 mg) was added at room temperature to a solution of 240 mg of p-methoxybenzyl (6R,7R)-7-[(Z)-2-methoxyimino-2-(2-tritylaminothiazol-4-yl)acetamido]-3-chloromethyl-3-cephem-4-carboxylate and 87 mg of triphenylphosphine in 5 ml of acetone, and the mixture was stirred for 1.5 hr. The reaction mixture was evaporated to dryness under reduced pressure, and 10 ml of methylene chloride was added thereto.

3-Methylimidazo[5,1-b]thiazole-2-carbaldehyde (150 mg) was added, and 15 ml of a 5% aqueous sodium hydrogencarbonate solution was added thereto. The reaction mixture was stirred at room temperature for 4 hr and then separated, and the aqueous layer was extracted with methylene chloride. The extract was combined with the organic layer, and the combined extract and organic layer were washed with a saturated saline solution, dried over anhydrous magnesium sulfate, and concentrated under reduced pressure. The concentrate was purified by Sephadex LH 20 column chromatography (eluent: chloroform:methanol=1:1) to give 225 mg (yield 82%) of the title compound.

NMR ($CDCl_3$) δ 2.33 (3H, s), 3.06 (1H, d, J=18 Hz), 3.45 (1H, d, J=18 Hz), 3.95 (1H, s), 4.07 (3H, s), 5.22 (2H, s), 6.36 (1H, d, J=12 Hz), 6.55 (1H, d, J=12 Hz), 7.00 (2H, s), 8.08 (1H, s)

Example 20

Sodium (6R,7R)-7-[(Z)-2-(2-aminothiazol-4-yl)-2-methoxyiminoacetamido]-3-[2-(3-methylimidazo[5,1-b]thiazol-2-yl)vinyl]-3-cephem-4-carboxylate (cis isomer)

The procedure of Example 2 was repeated, except that 225 mg of p-methoxybenzyl (6R,7R)-7-[(Z)-2- methoxyimino-2-(2-tritylaminothiazol-4-yl)acetamido]-3-[2-(3-methylimidazo[5,1-b]thiazol-2-yl)vinyl]-3-cephem-4-carboxylate (cis isomer) was used as the starting compound. Thus, 60.7 mg (yield 45%) of the title compound was obtained.

NMR (D$_2$O) δ 2.38 (3H, s), 3.42 (1H, d, J=18 Hz), 3.66 (1H, d, J=18 Hz), 3.98 (3H, s), 5.38 (1H, d, J=5 Hz), 5.84 (1H, d, J=5 Hz), 6.34 (1H, d, J=12 Hz), 6.56 (1H, d, J=12 Hz), 6.99 (1H, s), 7.02 (1H, s), 8.09 (1H, s)

Example 21 p-Methoxybenzyl (6R,7R)-7-[(Z)-2-ethoxyimino-2-(2-tritylaminothiazol-4-yl)acetamido]-3-[2-(3-methylimidazo[5,1-b]thiazol-2-yl)vinyl]-3-cephem-4-carboxylate (2:1 mixture of cis and trans isomers)

The procedure of Example 19 was repeated, except that 500 mg of p-methoxybenzyl (6R,7R)-7-[(Z)-2-ethoxyimino-2-(2-tritylaminothiazol-4-yl)acetamido]-3-chloromethyl-3-cephem-4-carboxylate was used as the starting compound. Thus, 416 mg (yield 73%) of the title compound was obtained.

NMR (CDCl$_3$) δ 1.33 (1H, t, J=7Hz), 1.36 (2H, t, 7 Hz), 2.38 (3H, s), 3.08 (2/3H, d, J=18 Hz), 3.42 (2/3H, d, J=18 Hz), 3.54 (1/3H, d, J=18 Hz), 3.67 (1/3H, d, J=18 Hz), 4.08 (3H, s), 4.26 (2/3H, q, J=7 Hz), 4.30 (4/3H, q, J=7 Hz), 5.24 (2H, s), 7.00 (1H, s), 7.23 (2/3H, s), 7.35 (1/3H, s), 8.33 (1/3H, s), 8.41 (2/3H, s)

Example 22

Sodium (6R,7R)-7-[(Z)-2-(2-aminothiazol-4-yl)-2-ethoxyiminoacetamido]-3-[2-(3-methylimidazo[5,1-b]thiazol-2-yl)vinyl]-3-cephem-4-carboxylate (2:1 mixture of cis and trans isomers)

The procedure of Example 2 was repeated, except that 208 mg of p-methoxybenzyl (6R,7R)-7-[(Z)-2-ethoxyimino-2-(2-tritylaminothiazol-4-yl)acetamido]-3-[2-(3-methylimidazo[5,1-b]thiazol-2-yl)vinyl]-3-cephem-4-carboxylate (a 2:1 mixture of cis and trans isomers) was used as the starting compound. Thus, 63.0 mg (yield 50%) of the title compound was obtained.

NMR (D$_2$O) δ 1.29 (1H, t, J=7 Hz), 1.31 (2H, t, J=7 Hz), 2.39 (1H, s), 2.42 (2H, s), 3.42 (2/3H, d, J=18 Hz), 3.67 (2/3H, d, J=18 Hz), 3.77 (1/3H, d, J=18 Hz), 3.88 (1/3H, d, J=18 Hz), 4.26 (3H, q, J=7Hz), 5.25 (1/3H, d, J=5 Hz), 5.39 (2/3H, d, J=5 Hz), 5.85 (1H, d, J=5 Hz), 6.40 (2/3H, d, J=11 Hz), 6.58 (2/3H, d, J=11 Hz), 6.82 (1/3H, d, J=15 Hz), 7.00 (1H, s), 7.05 (2/3H, d, J=15 Hz), 7.08 (1/3H, s), 7.16 (2/3H, s), 8.30 (1/3H, s), 8.35 (2/3H, s)

Example 23 p-Methoxybenzyl (6R,7R)-7-[(Z)-2-ethoxyimino-2-(2-tritylaminothiazol-4-yl)acetamido]-3-[2-(3,6-dimethylimidazo[5,1-b]thiazolium-2-yl)vinyl]-3-cephem-4-carboxylate iodide (2:1 mixture of cis and trans isomers)

The procedure of Example 5 was repeated, except that 208 mg of p-methoxybenzyl (6R,7R)-7-[(Z)-2-ethoxyimino-2-(2-tritylaminothiazol-4-yl)acetamido]-3-[2-(3-methylimidazo[5,1-b]thiazol-2-yl)vinyl]-3-cephem-4-carboxylate (a 2:1 mixture of cis and trans isomers) was used as the starting compound. Thus, 188 mg (yield 78%) of the title compound was obtained.

NMR (CDCl$_3$) δ 1.33 (3H, t, J=7Hz), 2.38 (3H, s), 3.10 (2/3H, d, J=18 Hz), 3.42 (2/3H, d, J=18 Hz), 3.55 (1/3H, d, J=18 Hz), 3.69 (1/3H, d, J=18 Hz), 4.08 (3H, s), 4.12 (3H, s), 4.26 (2H, q, J=7 Hz), 5.26 (2H, s), 7.00 (1H, s), 7.53 (2/3H, s), 7.55 (1/3H, s), 9.30 (1/3H, s), 9.38 (2/3H, s)

Example 24

(6R,7R)-7-[(Z)-2-(2-aminothiazol-4-yl)-2-ethoxyiminoacetamido]-3-[2-(3,6-dimethylimidazo[5,1-b]thiazolium-2-yl)vinyl]-3-cephem-4-carboxylate (2:1 mixture of cis and trans isomers)

The procedure of Example 2 was repeated, except that 188 mg of p-methoxybenzyl (6R,7R)-7-[(Z)-2-ethoxyimino-2-(2-tritylaminothiazol-4-yl)acetamido]-3-[2-(3,6-dimethylimidazo[5,1-b]thiazolium-2-yl)vinyl]-3-cephem-4-carboxylate iodide (a 1:2 mixture of cis and trans isomers) was used as the starting compound. Thus, 42.1 mg (yield 42%) of the title compound was obtained.

NMR (D$_2$O) δ 1.31 (3H, t, J=7 Hz), 2.51 (1H, s), 2.47 (2H, s), 3.44 (2/3H, d, J=18 Hz), 3.69 (2/3H, d, J=18 Hz), 3.76 (1/3H, d, J=18 Hz), 3.84 (1/3H, d, J=18 Hz), 3.86 (2/3H, d, J=18 Hz), 4.06 (3H, s), 4.27 (2H, q, J=7 Hz), 5.30 (1/3H, d, J=5 Hz), 5.40 (2/3H, d, J=5 Hz), 5.85 (1H, d, J=5 Hz), 6.49 (2/3H., d, J=11 Hz), 6.61 (2/3H, d, J=11 Hz), 6.86 (1/3H, d, J=15 Hz), 6.98 (1H, s), 7.01 (1/3H, s), 7.47 (2/3H, d, J=15 Hz), 7.52 (1/3H, s), 9.11 (1/3H, s), 9.15 (2/3H, s)

Example 25 p-Methoxybenzyl (6R,7R)-7-[(Z)-2-fluoromethoxyimino-2-(5-tritylamino-1,2,4-thiadiazol-3-yl)acetamido]-3-[2-(3-imidazo[5,1-b]thiazol-2-yl)vinyl]-3-cephem-4-carboxylate (2:1 mixture of cis and trans isomers)

The procedure of Example 19 was repeated, except that 240 mg of p-methoxybenzyl (6R,7R)-7-[(Z)-2-fluoromethoxyimino-2-(5-tritylamino-1,2,4-thiadiazol-3-yl)acetamido]-3-chloromethyl-3-cephem-4-carboxylate was used as the starting compound. Thus, 229 mg (yield 84%) of the title compound was obtained.

NMR (CDCl$_3$) 2.38 (3H, s), 3.11 (2/3H, d, J=18 Hz), 3.42 (2/3H, d, J=18 Hz), 3.52 (1/3H, d, J=18 Hz), 3.68 (1/3H, d, J=18 Hz), 4.12 (3H, s), 5.24 (2H, s), 5.83 (2H, d, J=55 Hz), 7.00 (1H, s), 7.08 (2/3H, s), 8.05 (1/3H, s), 8.30 (2/3H, s)

Example 26

Sodium (6R,7R)-7-[(Z)-2-(5-amino-1,2,4-thiadiazol-3-yl)-2-fluoromethoxyiminoacetamido]-3-[2-(imidazo[5,1-b]thiazol-3-yl)vinyl]-3-cephem-4-carboxylate (cis isomer) (trans isomer)

The procedure of Example 2 was repeated, except that 114 mg of p-methoxybenzyl (6R,7R)-7-[(Z)-2-fluoromethoxyimino-2-(5-tritylamino-1,2,4-thiadiazol-3-yl)acetamido]-3-[2-(3-imidazo[5,1-b]thiazol-2-yl)vinyl]-3-cephem-4-carboxylate (a 2:1 mixture of cis and trans isomers) was used as the starting compound. Thus, the title compound [cis isomer: 16.5 mg (yield 24%), trans isomer: 13.5 mg (yield 19%)] was obtained.

NMR (D$_2$O) (cis form) δ 2.39 (3H, s), 3.41 (1H, d, J=18 Hz), 3.66 (1H, d, J=18 Hz), 5.38 (1H, d, J=5 Hz), 5.83 (1H, d, J=55 Hz), 5.89 (1H, d, J=5 Hz), 6.37 (1H, d, J=11 Hz), 6.57 (1H, d, J=11 Hz), 7.07 (1H, s), 8.26 (1H, s) (trans form) δ 2.38 (3H, s), 3.73 (1H, d, J=18 Hz), 3.85 (1H, d, J=18 Hz), 5.35 (1H, d, J=5 Hz), 5.84 (1H, d, J=55 Hz), 5.90 (1H, d, J=5 Hz), 6.30 (1H, d, J=15 Hz), 6.82 (1H, d, J=15 Hz), 6.94 (1H, s), 8.02 (1H, s)

Example 27 p-Methoxybenzyl (6R,7R)-7-[(Z)-2-fluoromethoxyimino-2-(5-tritylamino-1,2,4-thiadiazol-3-yl)acetamido]-3-[2-(3,6-dimethylimidazo[5,1-b]thiazolium-2-yl)vinyl]-3-cephem-4-carboxylate iodide (cis isomer)

The procedure of Example 5 was repeated, except that 114 mg of p-methoxybenzyl (6R,7R)-7-[(Z)-2-fluoromethoxyimino-2-(5-tritylamino-1,2,4-thiadiazol-3-yl)acetamido]-3-[2-(3-imidazo[5,1-b]thiazol-2-yl)vinyl]-3-cephem-4-carboxylate (cis isomer) was used as the starting compound. Thus, 103 mg (yield 78%) of the title compound was obtained.

NMR (CDCl$_3$) 2.37 (3H, s), 3.11 (1H, d, J=18 Hz), 3.40 (1H, d, J=18 Hz), 4.09 (3H, s), 4.12 (3H, s), 5.23 (2H, s), 5.88 (2H, d, J=55 Hz), 7.44 (1H, s), 9.08 (1H, s)

Example 28

(6R,7R)-7-[(Z)-2-(5-Amino-1,2,4-thiadiazol-3-yl)-2-fluoromethoxyiminoacetamido]-3-[2-(3,6-dimethylimidazo[5,1-b]thiazolium-2-yl)vinyl]-3-cephem-4-carboxylate (cis isomer)

The procedure of Example 2 was repeated, except that 103 mg of p-methoxybenzyl (6R,7R)-7-[(Z)-2-fluoromethoxyimino-2-(5-tritylamino-1,2,4-thiadiazole-3-yl)acetamido]-3-[2-(3,6-dimethylimidazo[5,1-b]thiazolium-2-yl)vinyl]-3-cephem-4-carboxylate iodide (cis isomer) was used as the starting compound. Thus, 30.2 mg (yield 41%) of the title compound was obtained.

NMR (D$_2$O) δ 2.45 (3H, s), 3.43 (1H, d, J=18 Hz), 3.67 (1H, d, J=18 Hz), 4.06 (3H, s), 5.40 (1H, d, J=5 Hz), 5.85 (1H, d, J=55 Hz), 5.93 (1H, d, J=5 Hz), 6.40 (1H, d, J=11 Hz), 6.58 (1H, d, J=11 Hz), 7.50 (1H, s), 9.16 (1H, s)

Preparation Examples

Preparation for Injection

A pharmaceutical composition containing a compound according to the present invention is aseptically charged into vials so that each vial contains 1000 mg (potency) of the compound of the invention.

Capsule Preparation

Compound of the invention 250 parts (potency)

Milk sugar 60 parts (potency)

Magnesium stearate 5 parts (potency)

The above ingredients are homogeneously mixed, and the mixture is charged into capsules so that each capsule contains 250 mg (potency) of the compound of the invention.

Soft Capsule Preparation for Rectal Administration

Olive oil 160 parts

Polyoxyethylene lauryl ether 10 parts

Sodium hexametaphosphate 5 parts 25 parts (potency) of the compound of the present invention is added to and homogeneously mixed with a base comprising the above ingredients, and the mixture is charged into soft capsules for rectal administration so that each capsule may contain 250 mg (potency) of the compound of the invention.

Antibacterial Activity

The antibacterial activity of the compounds according to the present invention was assayed by the conventional two-fold dilution method. The minimum inhibitory concentrations (MIC) were as follows. The measurement was carried out in the following manner: $10^6$ CFU/ml of a bacterium to be tested was inoculated on a Medium N for disc susceptibility test (manufactured by Nissui Pharmaceutical Co., Ltd.), and cultivated at 35° C. for 18 to 20 hr.

TABLE 1

| Test strain | Trans isomer of Ex. 4 | Trans isomer of Ex. 14 | Cefdinir | Cefpirome |
|---|---|---|---|---|
| St. aureus 209PJC-1 | 0.20 | 0.20 | 0.20 | 0.39 |
| St. aureus M133 | 3.13 | 3.13 | 6.25 | 12.5 |
| St. aureus M126 | 12.5 | 6.25 | >100 | 50 |
| Ent. hirae ATCC8043 | 1.56 | 12.5 | 50 | 3.13 |
| Ent. faecalis W-73 | 0.78 | 3.13 | 25 | 25 |
| E. coli 255 | 0.78 | 0.10 | 50 | 0.20 |
| E. coli GN206 | 0.20 | <0.025 | 25 | <0.02 |
| 5M. morganii 1510 | 1.56 | 0.78 | 25 | 0.20 |
| E. cloacae G-0008 | 0.39 | 0.05 | 6.25 | 0.05 |
| Ser. marcescens No. 1 | 0.39 | 0.05 | 25 | 0.05 |

What is claimed is:

1. A cephem derivative represented by the formula (I):

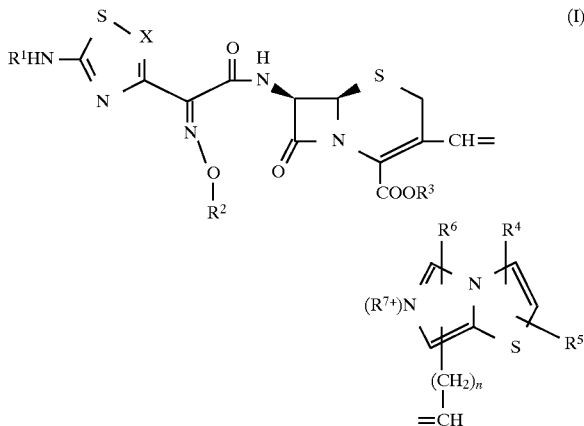

wherein X represents CH or N,

R$^1$ represents hydrogen or an amino protective group selected from the group consisting of alkoxycarbonyl, acyl and trityl, R$^2$ represents hydrogen; C$_{1-4}$ alkyl in which one or more hydrogen atoms may be substituted by halogen or carboxyl, C$_{1-4}$ alkoxycarbonyl, carbamoyl, N-C$_{1-4}$ alkylcarbamoyl, cyano, amino, or C$_{1-4}$ alkylamino; C$_{2-4}$ alkenyl; C$_{2-4}$ alkynyl; or C$_{3-6}$ cycloalkyl, R$^3$ is absent or represents hydrogen, a salt forming cation, or a carboxyl protective group selected from the group consisting of aryl, lower alkyl, lower alkoxymethyl, lower alkylthiomethyl, lower alkanoyloxymethyl, lower alkoxycarbonyloxyalkyl, lower alkylcarbonyloxyalkyl, and optionally substituted (2-oxo-1,3-dioxolen-4-yl)methyl, R$^4$, R$^5$, and R$^6$, which may be the same or different, each represent
hydrogen;
C$_{1-4}$ alkoxy;

$C_{1-4}$ alkylthio;
cyano;
carboxyl;
$C_{1-4}$ alkoxycarbonyl;
carbamoyl;
N-$C_{1-4}$ alkylcarbamoyl;
formyl;
amino in which one or more hydrogen atoms may be substituted by formyl, $C_{1-4}$ alkylcarbonyl, or $C_{1-4}$ alkylsulfonyl;
halogen;
$C_{1-4}$ alkyl in which one or more hydrogen atoms may be substituted by a group selected from the group consisting of hydroxyl, $C_{1-4}$ alkoxy, mercapto, $C_{1-4}$ alkylthio and cyano, halogen, carboxyl, $C_{1-4}$ alkoxycarbonyl, carbamoyl, N-$C_{1-4}$ alkylcarbamoyl, formyl, alkylcarbonyl, hydroxyimino, $C_{1-4}$ alkoxyimino, amino, formylamino, $C_{1-4}$ alkylcarbonylamino, halogen-substituted $C_{1-4}$ alkylcarbonylamino, carbamoyloxy, N-$C_{1-4}$ alkylcarbamoyloxy, $C_{1-4}$ alkylsulfonylamino, ureido, N—$C_{1-4}$ alkylureido, $C_{1-4}$ alkylcarbonylamino and imino $C_{1-4}$ alkylamino;
$C_{3-6}$ cycloalkyl;
$C_{2-4}$ alkenyl; or
$C_{2-4}$ alkynyl or
any two of $R^4$, $R^5$, and $R^6$ may together represent $C_{3-6}$ alkylene where one or more methylene groups in this alkylene group may be replaced by —NH—, —O—, —S—, or —CO—,
$R^{7+}$ is absent or represents a cation of $C_{1-6}$ alkyl, substituted $C_{1-6}$ alkyl, or substituted $C_{1-6}$ alkylene, and n is an integer of 0 to 1; or a pharmaceutically acceptable salt or ester thereof.

2. The compound according to claim 1, wherein $R^2$ represents hydrogen, $C_{1-4}$ alkyl in which one or more hydrogen atoms may be substituted by halogen or, $C_{3-6}$ cycloalkyl.

3. The compound according to claim 1, wherein $R^3$ represents a metabolically unstable carboxyl protective group.

4. The compound according to claim 1, wherein $R^3$ represents a cation of an alkali metal or an alkaline earth metal.

5. The compound according to claim 1, which is in the form of an intramolecular salt with $R^3$ being absent.

6. The compound according to claim 1, wherein $R^4$, $R^5$, or $R^6$ is $C_{1-4}$ alkyl optionally substituted by halogen.

7. The compound according to claim 6, wherein $C_{1-4}$ alkyl is present in the 2-, 3-, 5-, or 7-position of the imidazo[5,1-b]thiazolyl moiety.

8. The compound according to claim 1, wherein the imidazo[5,1-b]thiazolyl moiety is attached in its 3- or 2-position to the cephem skeleton.

9. A pharmaceutical composition comprising a compound according to any one of claims 2 to 8 or 1 together with a pharmaceutically acceptable carrier.

10. A method for treating an infectious disease caused by *Staphylococcus aureus* or *Enterococcus faecalis*, comprising administering an effective amount of a compound according to any one of claims 2 to 8 or 1 to a mammal.

11. The method according to claim 10, wherein the mammal is a human being.

* * * * *